(12) United States Patent
Lee et al.

(10) Patent No.: US 9,244,055 B2
(45) Date of Patent: Jan. 26, 2016

(54) MEASURING DEVICE

(71) Applicant: CERAGEM MEDISYS INC., Chungcheongnam-do (KR)

(72) Inventors: Jin Woo Lee, Chungcheongnam-do (KR); Jae Kyu Choi, Chungcheongnam-do (KR); Young Il Yoon, Chungcheongnam-do (KR)

(73) Assignee: Ceragem Medisys Inc. (KR)

( * ) Notice: Subject to any disclaimer, the term of this patent is extended or adjusted under 35 U.S.C. 154(b) by 0 days.

(21) Appl. No.: 14/406,343

(22) PCT Filed: Jun. 7, 2013

(86) PCT No.: PCT/KR2013/005049
§ 371 (c)(1),
(2) Date: Dec. 8, 2014

(87) PCT Pub. No.: WO2013/187638
PCT Pub. Date: Dec. 19, 2013

(65) Prior Publication Data
US 2015/0177220 A1   Jun. 25, 2015

(30) Foreign Application Priority Data
Jun. 14, 2012 (KR) .................... 10-2012-0063936

(51) Int. Cl.
*G01D 11/24* (2006.01)
*G01N 33/48* (2006.01)
*G01N 35/00* (2006.01)
*G01N 27/26* (2006.01)
(Continued)

(52) U.S. Cl.
CPC ............... *G01N 33/48* (2013.01); *G01N 27/26* (2013.01); *G01N 35/00029* (2013.01); *G01N 35/10* (2013.01); *G01N 33/487* (2013.01); *G01N 2035/00089* (2013.01); *G01N 2035/00108* (2013.01)

(58) Field of Classification Search
CPC .............................. G01D 11/24; G01D 11/245
USPC ............................................................ 73/431
See application file for complete search history.

(56) References Cited

U.S. PATENT DOCUMENTS

| 8,052,943 B2 | 11/2011 | Amano et al. |
| 2015/0014159 A1* | 1/2015 | Takeuchi ............. G01N 27/327 204/403.01 |
| 2015/0136818 A1* | 5/2015 | Tanizaki .......... G01N 33/48785 224/191 |

FOREIGN PATENT DOCUMENTS

| JP | 2003-042994 A | 2/2003 |
| KR | 10-2007-0073914 A | 7/2007 |
| KR | 10-2011-0095197 A | 8/2011 |

*Primary Examiner* — Lisa Caputo
*Assistant Examiner* — Jamel Williams
(74) *Attorney, Agent, or Firm* — Riverside Law LLP

(57) ABSTRACT

The present invention includes: a main body which defines a storage space in the lengthwise direction, and in which a plurality of biosensors can be stacked; a cover member covering one end of the storage space and including a discharge hole through which only one biosensor located at the outermost edge of the stacked biosensors can pass; and a cover coupled to the cover member in order to be raised and lowered so as to open and close the discharge hole. The discharge hole is closed such that the biosensors stacked in the storage space are not contaminated and the infiltration of impurities into the storage space is prevented, and the discharge hole is temporarily opened when the biosensors are to be used in order to withdraw the biosensors.

16 Claims, 10 Drawing Sheets

(51) Int. Cl.
*G01N 35/10* (2006.01)
*G01N 33/487* (2006.01)

MEASURING DEVICE

CROSS-REFERENCE TO RELATED APPLICATIONS

This application is the U.S. national phase application filed under 35 U.S.C. §371 claiming benefit to International Patent Application No. PCT/KR2013/005049, filed on Jun. 7, 2013, which is entitled to priority under 35 U.S.C. §119(a)-(d) to Korea application no. 10-2012-0063936, filed Jun. 14, 2012, each of which application is hereby incorporated herein by reference in its entirety.

TECHNICAL FIELD

The present invention relates to a measuring device using a biosensor, and more particularly, to an analysis device capable of sequentially discharging and analyzing a plurality of biosensors stacked therein.

BACKGROUND ART

A biosensor is a means which studies properties of a substance using a characteristic function of a living organism. Since a biomaterial such as blood sugar and ketone is used as a detection element, the biosensor has excellent sensitivity and reaction specificity. Therefore, the biosensor is used in extensive fields such as a clinical chemistry analysis in medical and pharmaceutical fields, a process measurement and an environment measurement in a biotechnology industry, and a safety evaluation of a chemical substance, and the fields are continuously being expanded. In particular, the biosensor is used in rapid disease diagnoses and various self-examinations such as a blood sugar measurement, a pregnancy diagnosis, and a urine examination.

In the case of the most common electrochemical biosensor, it is mainly used to measure the blood sugar. Here, an electrical signal is generated by an electrochemical reaction occurring when a specimen such as blood is introduced into the biosensor, and then transmitted to a measuring device connected or coupled with the biosensor.

In general, a plurality of biosensors may be packaged in a storage container or may be individually wrapped, and a user takes out the biosensors one by one, when an analyzing operation is performed, and inserts it into the measuring device.

However, in the conventional biosensor as described above, when the plurality of biosensors are individually packaged and then taken out one by one, if using, packaging costs necessary to manufacture a separate storage container are required. In the case in which an individually wrapped flat strip-shaped biosensor is opened and used, the packaging costs for individually packaging the biosensor are increased, and also when the user grasps the packaging with hands to use the biosensor, it is apprehended that the biosensor may be contaminated by the hands.

DISCLOSURE

Technical Problem

The present invention is directed to providing a measuring device in which a storage space configured to stack and store a plurality of biosensors is formed to be maintained airtightly and thus to prevent contamination of the biosensors due to foreign substances.

Also, the present invention is directed to providing a measuring device capable of enhancing a user's convenience.

Technical Solution

One aspect of the present invention provides a measuring device including a main body having a storage space formed therein in a lengthwise direction so that a plurality of biosensors are stacked; a covering member configured to cover one end of the storage space and having a discharge hole through which only one biosensor located at the outermost side of the stacked biosensors is discharged; a cover coupled to the covering member so as to be movable up and down and thus to open and close the discharge hole; and a pressing member having a pressing pin provided at a guide part to push and move the biosensor stacked in the storage space to a measurement position, the guide part being formed at an area of the main body to be parallel with the stacked biosensors, wherein the discharge hole is closed to seal the storage space, and the discharge hole is temporarily opened to discharge the biosensor.

A height of the discharge hole may be larger than a thickness of one biosensor, and may be smaller than a thickness of two stacked biosensors.

The covering member may have a through-hole which is formed at a position opposite to the discharge hole and in which the pressing pin is inserted.

An insertion hole in which the cover is inserted may be formed at the guide part, and a lifting protrusion may protrude around an inner side of the insertion hole, and a short stepped portion configured to protrude so as to form an inclined surface in contact with the lifting protrusion may be formed at an outer circumferential surface of the cover formed in a cylindrical shape.

An elastic member may be installed between the cover and the covering member to press the inclined surface toward the lifting protrusion.

The pressing member may include an upper end surface having a cut groove which is formed to be cut in a lengthwise direction and in which the cover is inserted; side end surfaces which are vertically bent from both sides of the upper end surface; and a sliding rod formed at a center area of the upper end surface to protrude in the same direction as the side end surfaces and having the pressing pin configured to protrude from an end thereof so as to be inserted into a through-hole formed in the covering member.

A rack gear part may be formed at one side surface of a cut groove of the upper end surface, and a pinion gear part engaged with the rack gear part may be formed at an outer circumferential surface of the cover.

A guide groove in which the sliding rod is guided may be formed at the guide part.

A moving means configured to move the pressing member along the guide part may be installed at the guide part.

The moving means may include a rack gear formed at one side surface of the pressing pin, and a driving motor in which a pinion gear engaged with the rack gear is installed.

A discharge part through which an end of the measurement position is in communication with an outer side may be formed at the main body, and a display part configured to display measured information or alert signal may be provided at one side surface thereof.

A sensor configured to detect an opening state of the discharge hole may be installed at a discharge hole side of the covering member.

A stopper configured to protrude toward the pressing member may be provided at the guide part, and a stopping groove in which the stopper is temporarily inserted may be provided at the pressing member, and the pressing member may be temporarily stopped in a state in which the biosensor is located at the measurement position.

A stopper configured to protrude toward the pressing member may be provided at the guide part, and a stopping groove may be provided at the pressing member so that the stopper is temporarily inserted in a state in which the pressing pin locates the biosensor at the measurement position.

A lifting member configured to press the biosensor toward the covering member may be installed at the storage space.

The lifting member may include a lifting plate slidably inserted into the storage space to support the biosensors; an elastic member configured to press the lifting plate toward the covering member; and a cap configured to cover other opening portion of the storage space and to support the elastic member.

A packing may be installed at the cover to enhance airtightness of an opening/closing portion configured to open and close the discharge hole.

Advantageous Effects

According to the measuring device of the present invention, as described above, since the storage space in which the plurality of biosensors are stacked is formed in the measuring device so that the biosensors are discharged one by one by the simple operation, it is possible to enhance the user's convenience and also to reduce the manufacturing costs.

Also, according to the measuring device of the present invention, since the approach of the contaminants is blocked, while the biosensors stacked in the storage space are mechanically discharged and then moved to the measurement position, it is possible to enhance the reliability of measured values and the operability.

Also, according to the measuring device of the present invention, since the storage space of the biosensors can be airtightly maintained, it is possible to prevent deterioration of the biosensors and to ensure a long period of usage.

DESCRIPTION OF DRAWINGS

FIG. 5 is a constitution view illustrating a state in which the cover is locked.

FIG. 6 is a constitution view illustrating a state in which the cover is unlocked.

FIG. 7 is a constitution view illustrating a state in which the biosensor is moved to a measurement position.

FIG. 8 is a constitution view illustrating a state in which the biosensor is removed.

MODES OF THE INVENTION

Hereinafter, a measuring device according to preferred embodiments of the present invention will be described in detail with reference to the accompanying drawings.

Figure 1:
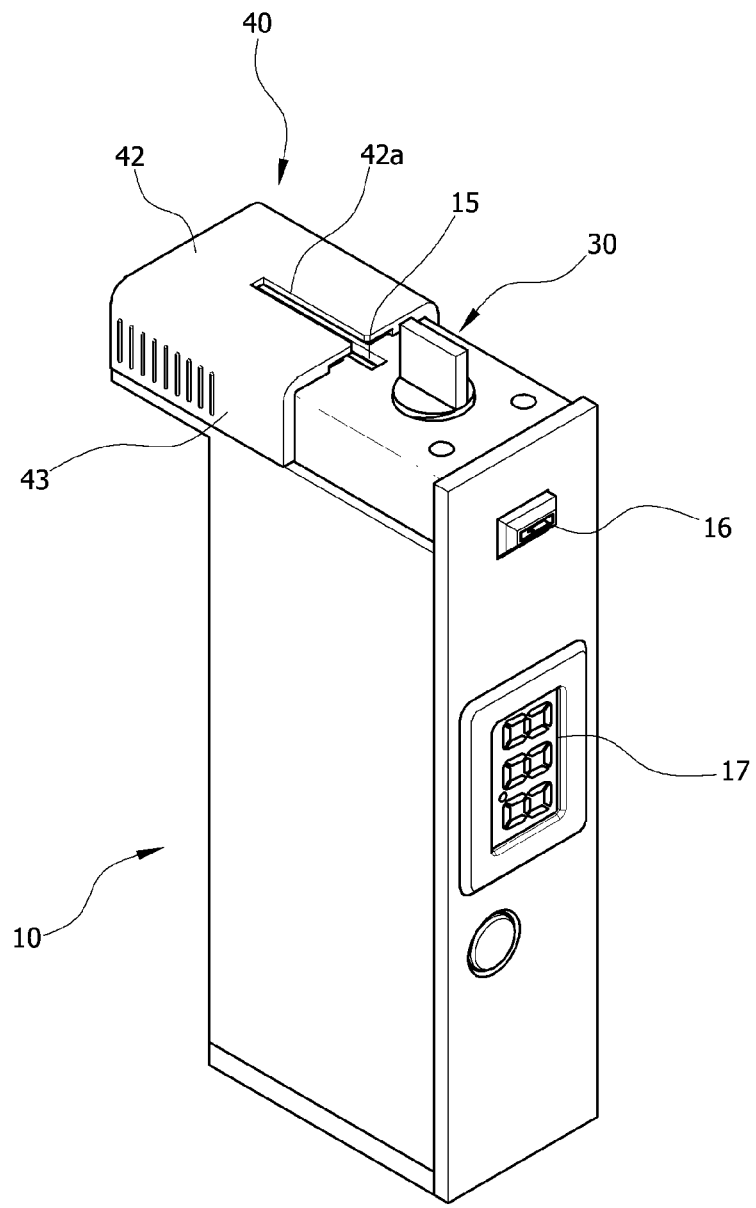
FIG. 1 is a perspective view of a measuring device according to a first embodiment of the present invention.
Figure 2:
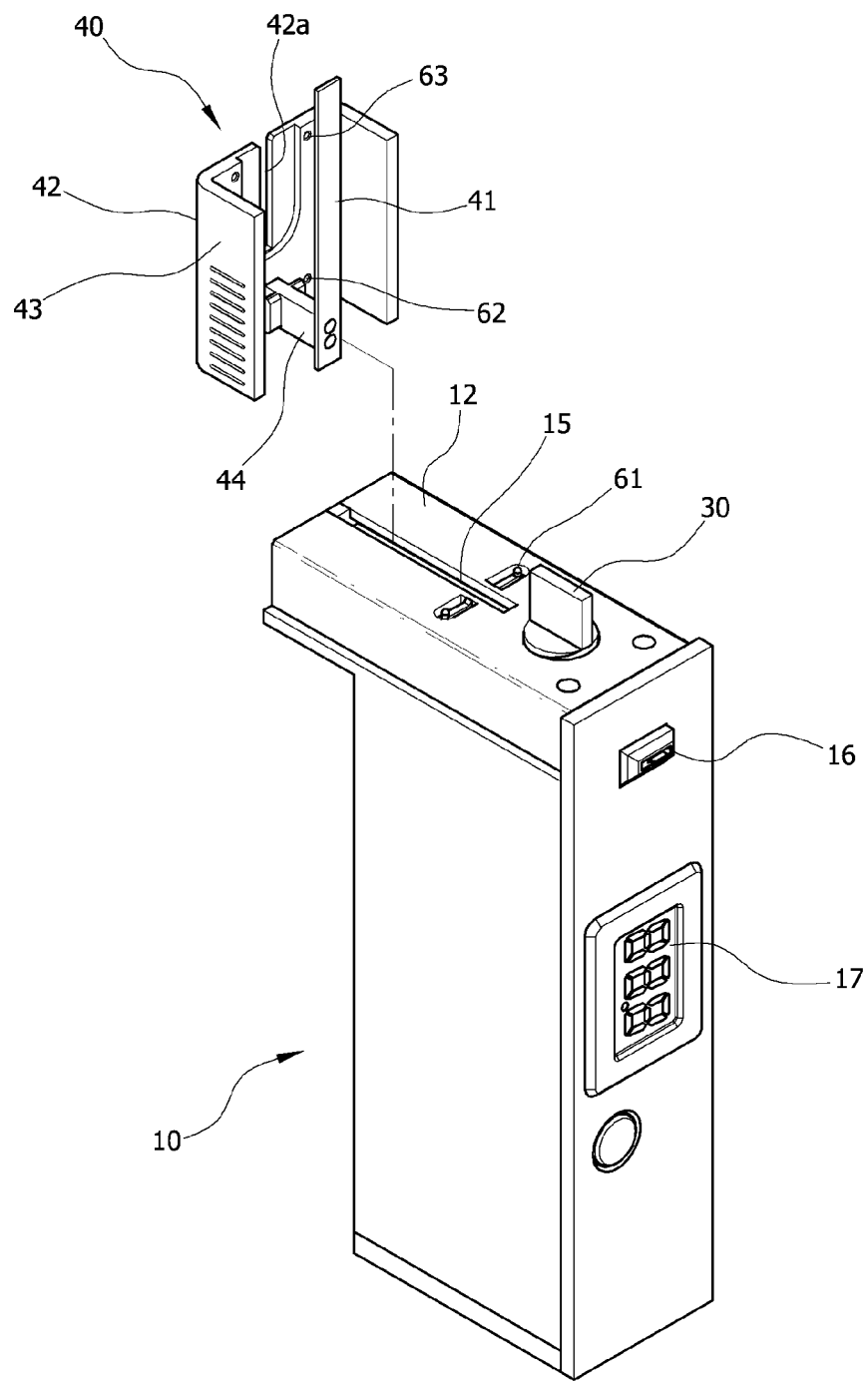
FIG. 2 is an exploded perspective view illustrating a state in which the measuring device of FIG. 1 is partially disassembled.
Figure 3:
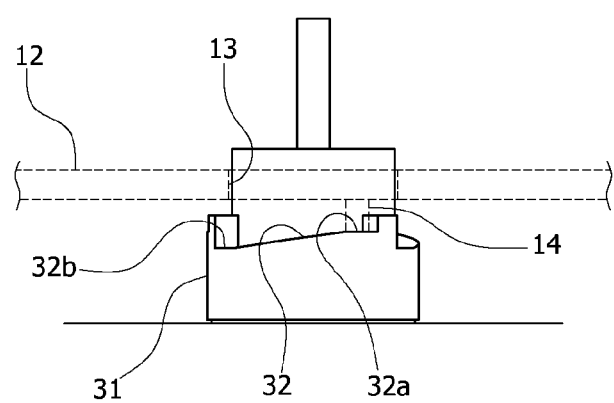
FIG. 3 is a constitution view illustrating a state in which a cover closes a discharge hole.
Figure 4:
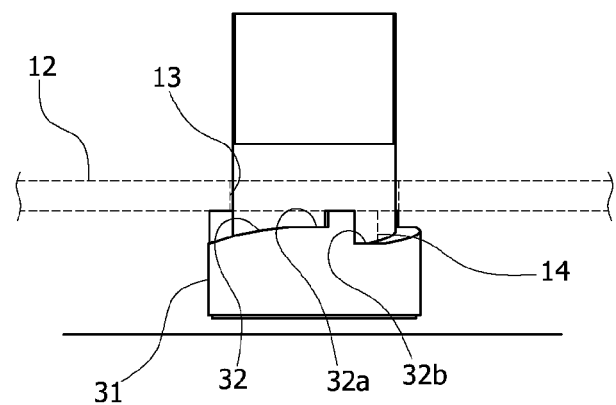
FIG. 4 is a constitution view illustrating a state in which the cover opens the discharge hole.
Figure 5:
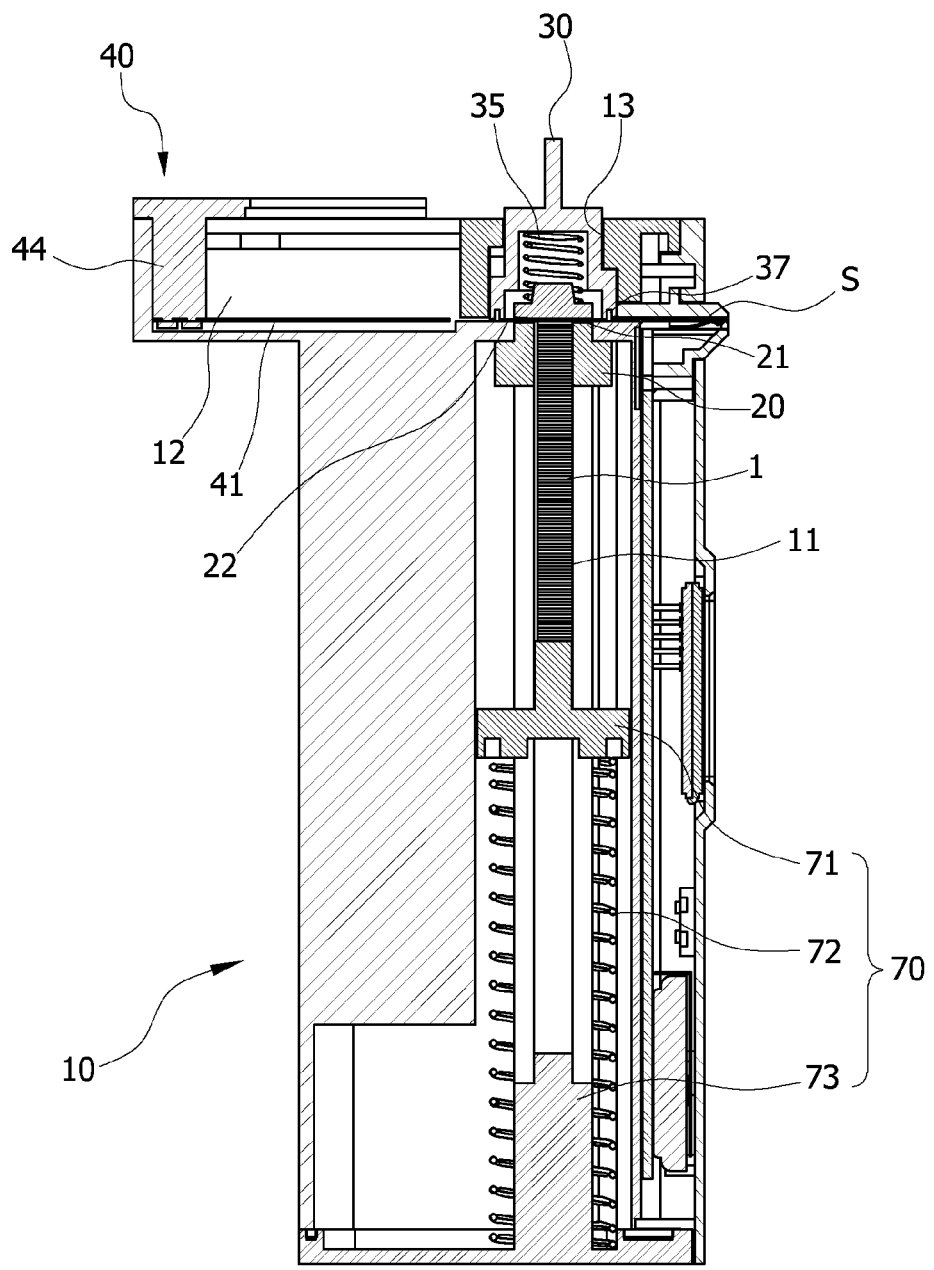
FIGS. 5 to 8 are constitution views illustrating, step-by-step, states in which the measuring device is operated.
Figure 6:
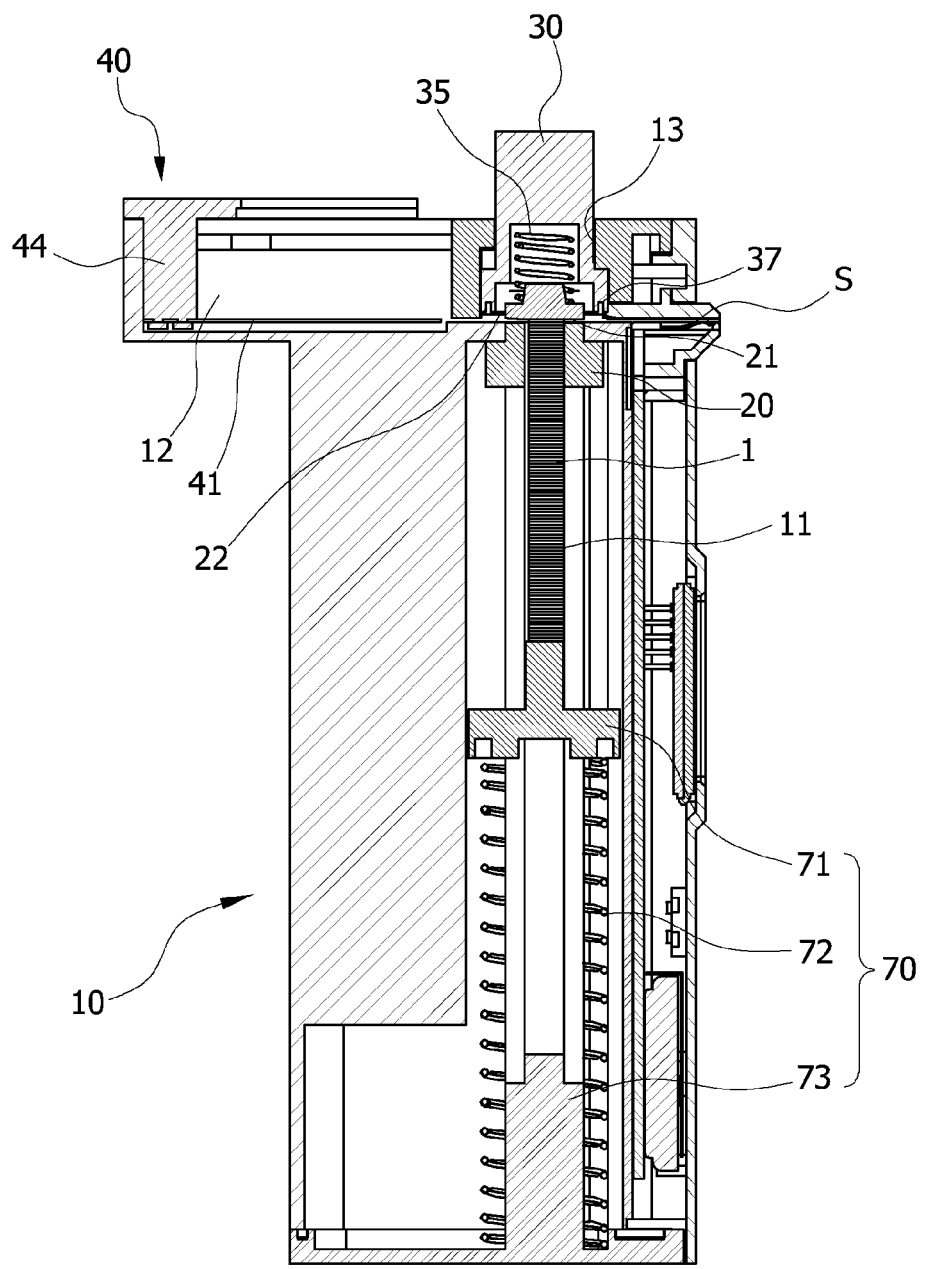
Figure 7:
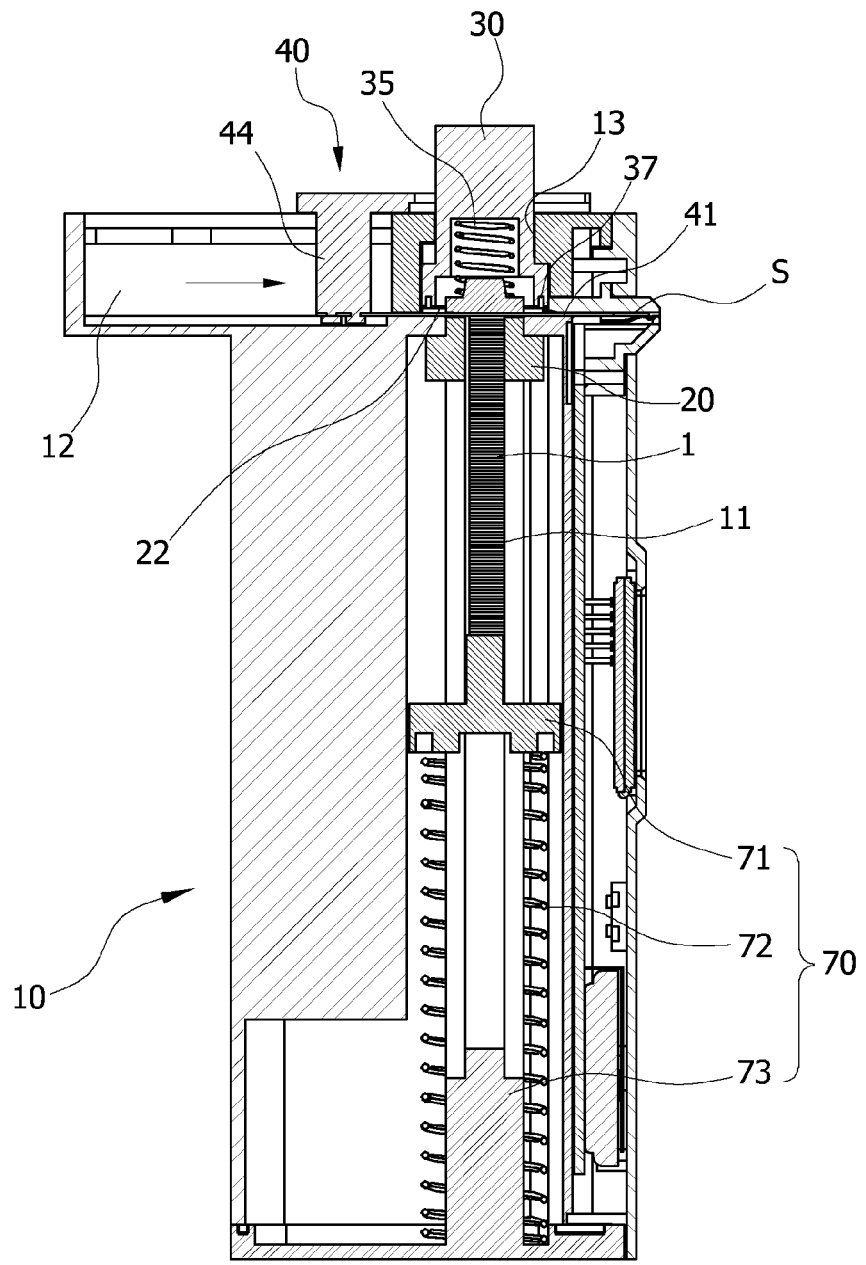
Figure 8:
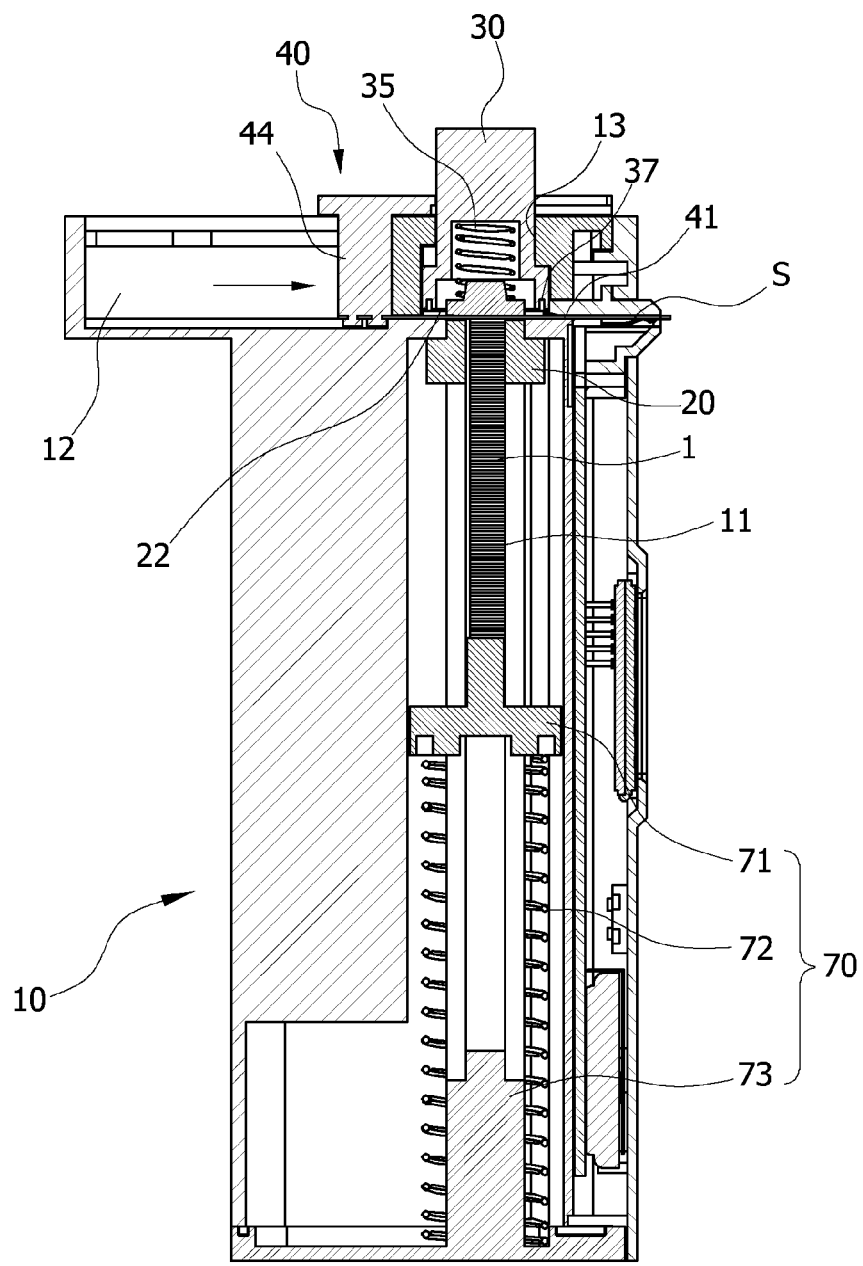

FIG. 1 is a perspective view of a measuring device according to a first embodiment of the present invention, FIG. 2 is an exploded perspective view illustrating a state in which the measuring device of FIG. 1 is partially disassembled, FIG. 3 is a constitution view illustrating a state in which a cover closes a discharge hole, FIG. 4 is a constitution view illustrating a state in which the cover opens the discharge hole, FIGS. 5 to 8 are constitution views illustrating, step-by-step, states in which the measuring device is operated, FIG. 5 is a constitution view illustrating a state in which the cover is locked, FIG. 6 is a constitution view illustrating a state in which the cover is unlocked, FIG. 7 is a constitution view illustrating a state in which the biosensor is moved to a measurement position, and FIG. 8 is a constitution view illustrating a state in which the biosensor is removed.

As illustrated in FIGS. 1 to 8, the measuring device according to a first embodiment of the present invention includes a main body 10 having a storage space 11 formed therein so that a plurality of biosensors 1 are stacked, a covering member 20 installed at the main body 10 to cover one side of the storage space 11 and having a discharge hole 21 through which the biosensor 1 is discharged, a cover 30 coupled to the covering member 20 so as to open and close the discharge hole 21, and a pressing member 40 installed at a guide part 12 formed at one side of the main body 10 to be slidable.

The main body 10 is formed in a hexahedral shape, and the storage space 11 is formed in an internal space thereof in a lengthwise direction thereof. A discharge part 16 through which the biosensor 1 is discharged is formed at one side thereof, and a display part 17 is formed at a lower end side thereof.

A lifting member 70 which presses the biosensors 1 toward the covering member 20 is installed at the storage space 11. The lifting member 70 includes a lifting plate 71 which is inserted into the storage space 11 to be slidable, an elastic member 72 which elastically supports the lifting plate 71 and presses the lifting plate 71 toward the covering member 20, and a cap 73 which is installed at a lower surface of the main body 10 to cover other opening portion of the storage space 11 and configured to support the elastic member 72. The elastic member 72 is preferably configured with a compression spring.

A guide part 12 which extends in a direction perpendicular to the lengthwise direction is formed at one end of an upper side of the main body 10. The guide part 12 is preferably formed to be parallel with the biosensors 1 stacked in the storage space 11. A guide groove 15 is formed at the guide part 12 to extend along a center portion thereof. Further, a predetermined portion of an upper end surface of the guide part 12 is cut away to have elasticity, and a stopper 61 is provided at a center of the cut portion to protrude toward the pressing member 40. The stopper 61 is temporarily inserted into stopping grooves 62 and 63 formed at an inner side of an upper end surface 42 of the pressing member 40 to be described later. When the pressing member 40 is located at an initial position before an operation thereof, the stopper 61 is inserted into the stopping groove 63 formed at one side, such that the pressing member 40 may be temporarily maintained in a stopped state. Further, at a moment when the biosensor 1 is located at a measurement position S, the stopper 61 is inserted into the stopping groove 62 formed at the other side, such that the pressing member 40 may be temporarily maintained in the stopped state. An insertion hole 13 in which the cover 30 is inserted is formed at the guide part 12 to pass therethrough in the lengthwise direction of the main body 10. A lifting protrusion 14 is formed around an inner side of the insertion hole 13 to protrude toward a lower end thereof. The number of lifting protrusions 14 is the same as the number of inclined surfaces 32 to be described later.

The covering member 20 configured to cover one opening portion of the storage space 11 of the main body 10 is formed in a cylindrical shape inserted into the one opening portion of the storage space 11. A through-cavity which is in communication with the storage space 11 is formed at a center portion of the covering member 20 so that the biosensors 1 may be stacked therein, and a through-hole 22 and the discharge hole 21 are formed at an end of the through-cavity to be symmetric with respect to a center point. The discharge hole 21 has an inner diameter corresponding to a cross-sectional area of the biosensor 1 so that only one biosensor 1 may pass. At this time, it is preferable that a width of the discharge hole 21 is formed to be larger than that of the biosensor 1, and a height of the discharge hole 21 is larger than a thickness of one biosensor 1, but smaller than a thickness of two stacked biosensors 1. Further, the covering member 20 may be formed as a separate member. However, it is preferable that the covering member 20 is integrally formed with the main body 10 or the storage space 11.

The cover 30 is formed in a cylindrical shape which covers an upper end of the covering member 20. Preferably, a handle may be formed at an end of one side thereof to be easily grasped by a user. An insertion space which is opened toward an end surface of the other side is formed at a center portion of the cover 30, and an elastic member 35 of which one surface is supported by the covering member 20 is inserted into the insertion space. The elastic member 35 is pressed toward an upper end of the cover 30. A short stepped portion 31 having the inclined surfaces 32 in contact with the lifting protrusion 14 is formed at an outer circumferential surface of the cover 30. The short stepped portion 31 has a larger outer diameter than an outer diameter of the upper end side of the cover 30. If an image of the inclined surface 32 is projected from a front side thereof, the inclined surface 32 forms an upper end surface of the short stepped portion 31, and connects a top dead point 32a having a high horizontal position with a bottom dead point 32b having a low horizontal position. The elastic member 35 presses the inclined surface 32 toward the lifting protrusion 14. Further, a packing 37 is installed at the cover 30 to enhance airtightness at a lower surface of an opening/closing portion configured to open and close the discharge hole 21. The packing 37 is formed in a circular ring shape, and serves to block an inner side of the storage space 11 and thus to prevent foreign substances or moisture from being introduced into the storage space 11.

The pressing member 40 includes an upper end surface 42 having a cut groove 42a which is formed to be cut in a lengthwise direction and in which the cover 30 is inserted, side end surfaces 43 which are vertically bent from both sides of the upper end surface 42, a sliding rod 44 which is formed at a center area of the upper end surface 42 to protrude in the same direction as the side end surfaces 43, and a plate-shaped pressing pin 41 which is installed at an end of the sliding rod 44 to protrude toward the through-hole 22. The sliding rod 44 is slidably coupled into the guide groove 15 formed to be cut along a center portion of the guide part 12.

Further, a sensor 36 is installed at a position of the discharge hole 21 side of the covering member 20, which is in contact with the cover 30. The sensor 36 is a contact sensor which detects whether to be in contact with the cover 30 and thus an opening/closing state of the discharge hole 21. The opening/closing state may be displayed on the display part 17 based on an opening/closing signal detected by the sensor 36, or an alert sound or alert light may be generated, such that the user may recognize it.

An operation of the measuring device according to the first embodiment of the present invention, as described above, will be described in detail.

First, before the measuring device is operated, the biosensors 1 have to be installed. To this end, the cap 73 is opened, a predetermined number of biosensors 1 are inserted into the storage space 11, the lifting plate 71 and the elastic member 72 are inserted in turn, and then the cap 73 is closed. Therefore, the plurality of biosensors 1 stacked in the storage space 11 are pressed toward the covering member 20 by an elastic force of the elastic member 72.

As illustrated in FIG. 5, in a state in which the plurality of biosensors 1 are stacked in the storage space 11, if it is intended that one biosensor 1 is moved to the measurement position S and a measuring operation is started, the cover 30 maintained to close the discharge hole 21, as illustrated in FIG. 6, should be opened.

As illustrated in FIGS. 3 and 5, in an initial state, the lifting protrusion 14 should be maintained to be in contact with the top dead point 32a of the inclined surface 32, and thus the cover 30 is maintained to be moved down. Therefore, since the discharge hole 21 and the through-hole 22 are closed by the cover 30, the storage space 11 is maintained to be closed, and thus the foreign substances are prevented from being introduced.

In this situation, when the handle of the cover 30 is grasped and then turned toward one side, the cover 30 is moved up along the inclined surface 32 by the force of the elastic member 35, and the lifting protrusion 14 which is in contact with the top dead point 32a is switched to be in contact with the bottom dead point 32b. As the cover 30 is moved up, the discharge hole 21 and the through-hole 22 are opened.

When the cover 30 is rotated and the discharge hole 21 and the through-hole 22 are opened, the pressing member 40 is pushed and moved to one side, as illustrated in FIG. 7.

The sliding rod 44 of the pressing member 40 is guided along the guide groove 15. When movement of the pressing member 40 is performed, the pressing pin 41 formed at the end of the sliding rod 44 is moved, passes through the through-hole 22, and then pushes and moves the biosensor 1 located at the uppermost side of the storage space 11 toward the discharge hole 21. Then, the biosensor 1 is pushed and moved to the measurement position S via the discharge hole 21 by the pressing pin 41. When the biosensor 1 is moved to the measurement position, the stopper 61 formed at the guide part 12 is temporarily inserted into the stopping groove 62, and thus the movement of the pressing member 40 is temporarily stopped.

While the movement of the pressing member 40 is temporarily stopped, the biosensor 1 is located at the measurement position S. A recognition electrode is provided at the measurement position S. The recognition electrode may be configured with at least two spring pins, and may perform recognition of the insertion of the biosensor 1, recognition of whether a proper amount of specimen is injected, recognition of a code key, an electric connection between the biosensor 1 and a measuring circuit, or the like. At the measurement position S, one part of the biosensor 1 may be in contact with a socket to be electrically connected with the measuring device, and the other part may be exposed to an outer side through the discharge hole 21 so as to absorb a specimen.

When measurement and analysis (qualitative or quantitative analysis) of the biosensor 1 are completed at the measurement position S, a force is applied to the pressing member 40 so that the pressing member 40 is further moved in the same direction, as illustrated in FIG. 8. At this time, the stopper 61 is released from the stopping groove 62 by the applied force. The biosensor 1 is pushed by the pressing pin 41 and then discharged to an outer side of the main body 10 through the discharge part 16.

When the discharging of the biosensor 1 is completed, the pressing member 40 is returned to the initial position, and then the cover 30 which is moved up is rotated reversely to be moved down. The discharge hole 21 and the through-hole 22 are closed by the cover 30 which is moved down. The packing 37 installed at the cover 30 is in close contact with the lower surface of the guide part 12, and thus the airtightness of the storage space 11 is enhanced.

In the measuring device of the present invention, as described above, since the biosensors 1 are stacked in the storage space 11 of the measuring device, and the storage space 11 is maintained airtightly, contamination thereof due to the foreign substances may be prevented, and thus the packaging costs of each biosensor 1 may be reduced. Further, a strip installation may be easily performed by only a mechanical operation without separately removing of the packaging or inserting of a strip into an injection port, and thus the user's convenience is enhanced.

Further, since the present invention has a structure in which the discharge hole 21 is temporarily opened and the biosensor 1 is moved to the measurement position S by the pressing pin 41, the biosensor 1 may be prevented from being contaminated by the foreign substances, and thus stability of the measuring device, and the reliability of measured values may be enhanced.

Figure 9:
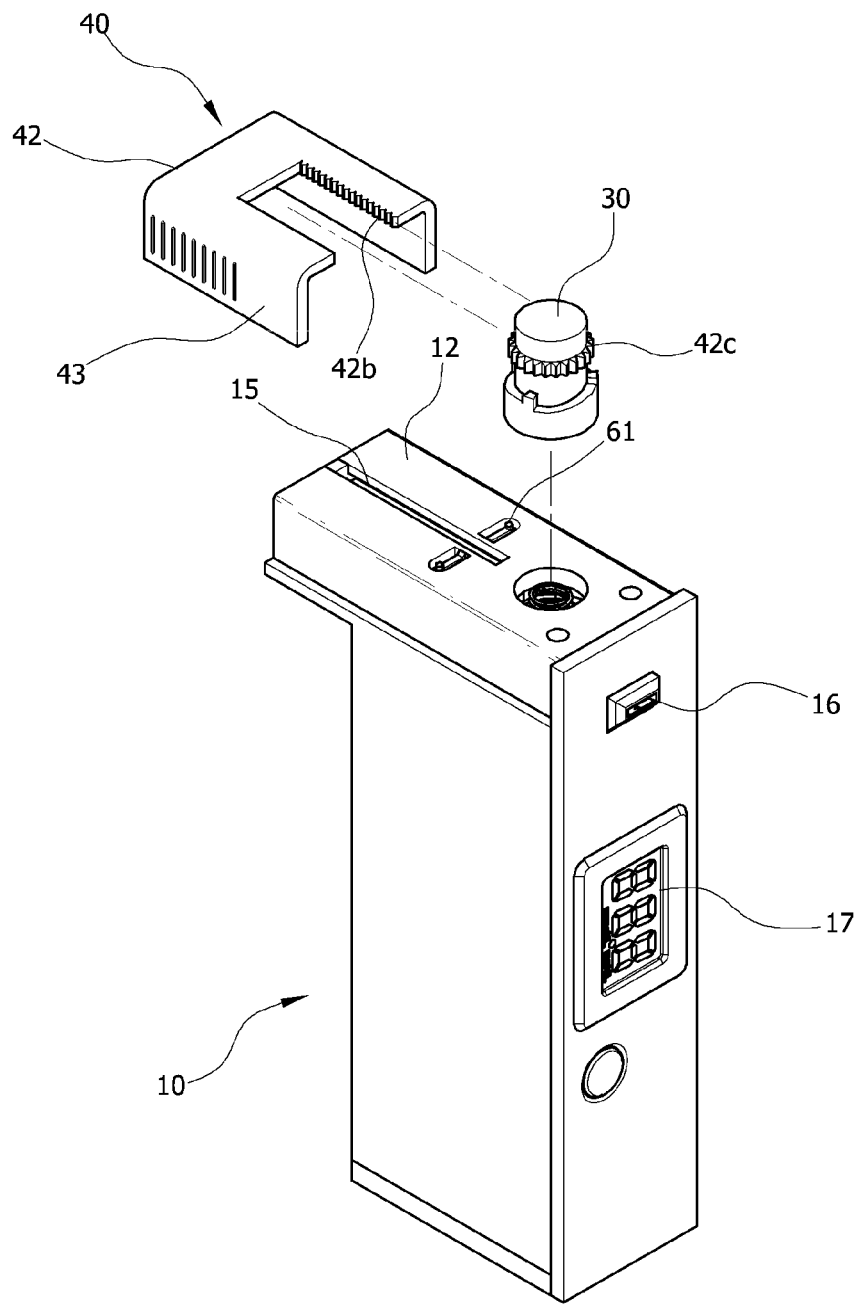
FIG. 9 is an exploded perspective view of a measuring device according to a second embodiment of the present invention.

In the same way, as illustrated in FIG. 9, in a measuring device according to a second embodiment of the present invention, a pinion gear part 42c is formed along an outer circumferential surface of an upper end side of a cylindrical portion of the cover 30, and a rack gear part 42b is formed at one side surface of both side surfaces of a cut groove 42a formed to be cut, such that the cover 30 is inserted therein.

As described above, since the rack gear part 42b and the pinion gear part 42c are engaged with each other, the pinion gear part 42c engaged with the rack gear part 42b is rotated, when the pressing member 40 is moved by the user, and the cover 30 is moved up, as illustrated in FIGS. 3 and 4, and the discharge hole 21 and the through-hole 22 are opened, and thus the biosensor 1 is moved.

The other parts except the structure in which the rack gear part 42b and the pinion gear part 42c are additionally formed, and the operation thereof are the same as those in the first embodiment.

Figure 10:
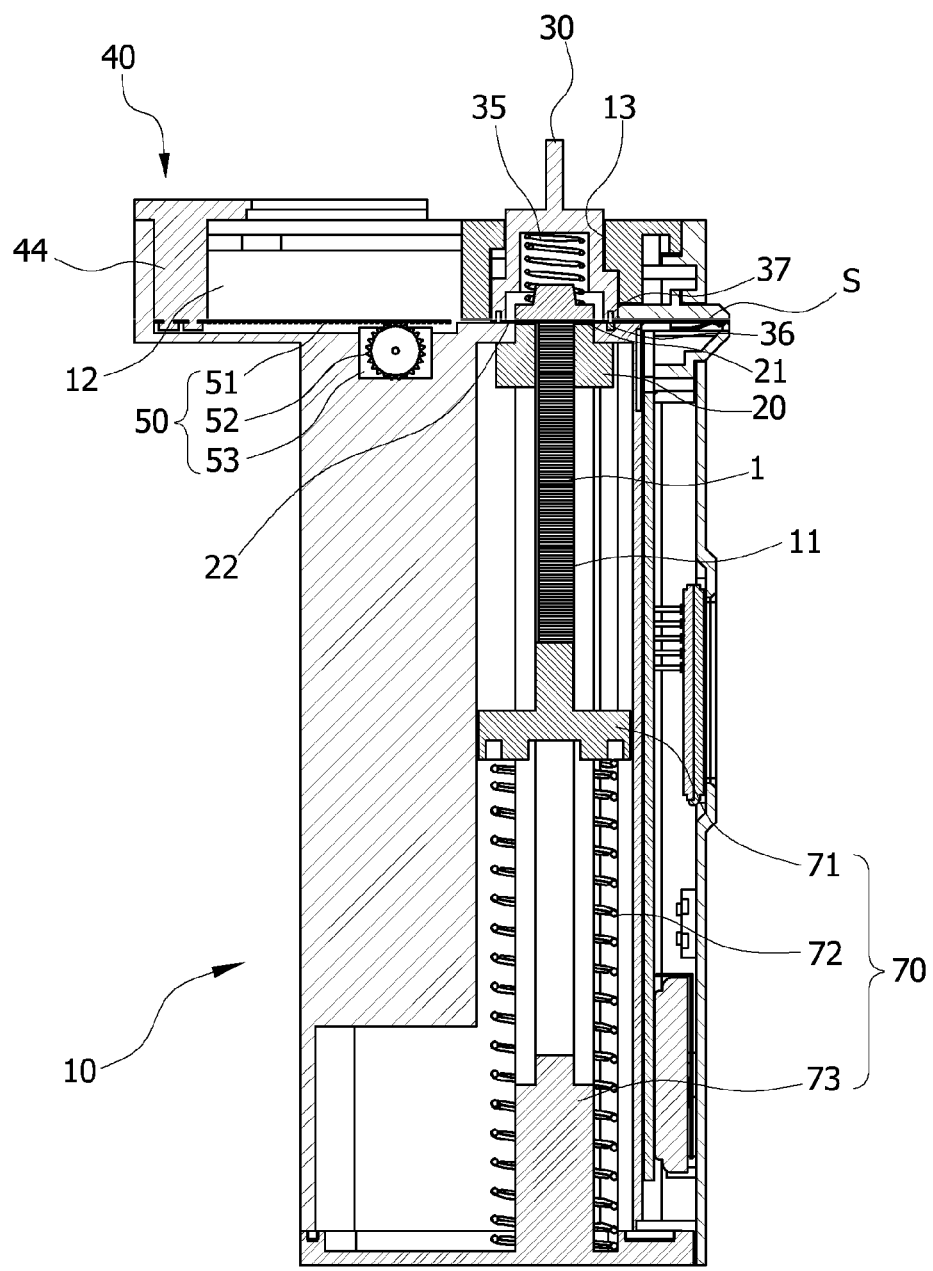
FIG. 10 is a cross-sectional view of a measuring device according to a third embodiment of the present invention.

In the same way, as illustrated in FIG. 10, in a measuring device according to a third embodiment of the present invention, a moving means 50 configured to move the pressing member 40 is installed at the guide part 12.

The moving means 50 includes a rack gear 51 formed at one side surface of the pressing pin 41, and a driving motor 53 in which a pinion gear 52 engaged with the rack gear 51 is installed. The moving means 50 may use various driving methods, such as a cylinder having a piston, other than the driving motor 53, as long as the pressing member 40 may be moved.

When the driving motor 53 is driven by operating an operation button formed at a predetermined position of an outer circumferential surface of the main body 10 or operating an operating part displayed on the display part 17 in a touch manner, the pinion gear 52 is rotated, and the rack gear 51 engaged with the pinion gear 52 is interlocked, and thus the pressing member 40 is moved.

In the measuring device according to the third embodiment of the present invention, the other parts except the structure in which the moving means 50 is additionally installed to automatically operate the pressing member 40 which was manually operated, and the operation thereof are the same as those in the first and second embodiments.

Although a few embodiments of the present invention have been shown and described, it would be appreciated by those skilled in the art that changes may be made in these embodiments without departing from the principles and spirit of the invention, the scope of which is defined in the claims and their equivalents.

The invention claimed is:

1. A measuring device comprising:
   a main body having a storage space formed therein in a lengthwise direction so that a plurality of biosensors are stacked;
   a covering member configured to cover one end of the storage space and having a discharge hole through which only one biosensor located at the outermost side of the stacked biosensors is discharged;
   a cover coupled to the covering member so as to be movable up and down and thus to open and close the discharge hole; and
   a pressing member having a pressing pin provided at a guide part to push and move the biosensor stacked in the storage space to a measurement position S, the guide part being formed at an area of the main body to be parallel with the stacked biosensors,
   wherein the discharge hole is closed to seal the storage space, and the discharge hole is temporarily opened to discharge the biosensor.

2. The device of claim 1, wherein a height of the discharge hole is larger than a thickness of one biosensor, and is smaller than a thickness of two stacked biosensors.

3. The device of claim 2, wherein the covering member has a through-hole which is formed at a position opposite to the discharge hole and in which the pressing pin is inserted.

4. The device of claim 2, wherein an insertion hole in which the cover is inserted is formed at the guide part, and a lifting protrusion protrudes around an inner side of the insertion hole, and a short stepped portion configured to protrude so as to form an inclined surface in contact with the lifting protrusion is formed at an outer circumferential surface of the cover formed in a cylindrical shape.

5. The device of claim 4, wherein an elastic member is installed between the cover and the covering member to press the inclined surface toward the lifting protrusion.

6. The device of claim 2, wherein the pressing member comprises:
   an upper end surface having a cut groove which is formed to be cut in a lengthwise direction and in which the cover is inserted;
   side end surfaces which are vertically bent from both sides of the upper end surface; and
   a sliding rod formed at a center area of the upper end surface to protrude in the same direction as the side end surfaces and having the pressing pin configured to protrude from an end thereof so as to be inserted into a through-hole formed in the covering member.

7. The device of claim 6, wherein a rack gear part is formed at one side surface of a cut groove of the upper end surface, and a pinion gear part engaged with the rack gear part is formed at an outer circumferential surface of the cover.

8. The device of claim 6, wherein a guide groove in which the sliding rod is guided is formed at the guide part.

9. The device of claim 7, wherein a moving means configured to move the pressing member along the guide part is installed at the guide part.

10. The device of claim 9, wherein the moving means comprises a rack gear formed at one side surface of the pressing pin, and a driving motor in which a pinion gear engaged with the rack gear is installed.

11. The device of claim 2, wherein a discharge part through which an end of the measurement position S is in communication with an outer side is formed at the main body, and a display part configured to display measured information or alert signal is provided at one side surface thereof.

12. The device of claim 11, wherein a sensor configured to detect an opening state of the discharge hole is installed at a discharge hole side of the covering member.

13. The device of claim 2, wherein a stopper configured to protrude toward the pressing member is provided at the guide part, and a stopping groove in which the stopper is temporarily inserted is provided at the pressing member, and the pressing member is temporarily stopped in a state in which the biosensor is located at the measurement position S.

14. The device of claim 1, wherein a lifting member configured to press the biosensor toward the covering member is installed at the storage space.

15. The device of claim 14, wherein the lifting member comprises:
- a lifting plate slidably inserted into the storage space to support the biosensors;
- an elastic member configured to press the lifting plate toward the covering member; and
- a cap configured to cover other opening portion of the storage space and to support the elastic member.

16. The device of claim 1, wherein a packing is installed at the cover to enhance airtightness of an opening/closing portion configured to open and close the discharge hole.

* * * * *